United States Patent [19]
Chen et al.

[11] Patent Number: 5,690,691
[45] Date of Patent: Nov. 25, 1997

[54] GASTRO-INTESTINAL PACEMAKER HAVING PHASED MULTI-POINT STIMULATION

[75] Inventors: Jian Dez Chen, Edmond, Okla.; Richard W. McCallum, Charlottesville, Va.; Ronald Williams, Charlottesville, Va.; Robert Ross, Charlottesville, Va.; Zhiyue Lin, Charlottesville, Va.; Jonathan Tillack, Charlottesville, Va.

[73] Assignee: The Center for Innovative Technology, Herndon, Va.

[21] Appl. No.: 646,959

[22] Filed: May 8, 1996

[51] Int. Cl.$^6$ ..................... A61N 1/32
[52] U.S. Cl. .............. 607/40; 607/133; 607/148; 607/72
[58] Field of Search ................ 607/2, 40, 72, 607/116, 133, 148; 600/29, 30

[56] References Cited

U.S. PATENT DOCUMENTS

| | | |
|---|---|---|
| 3,411,507 | 11/1968 | Wingrove . |
| 4,628,928 | 12/1986 | Lowell . |
| 4,703,755 | 11/1987 | Tanagho et al. ............ 607/40 |
| 4,921,481 | 5/1990 | Danis et al. . |
| 5,188,104 | 2/1993 | Wernicke et al. . |
| 5,197,491 | 3/1993 | Anderson et al. . |
| 5,292,344 | 3/1994 | Douglas .................... 607/40 |
| 5,358,513 | 10/1994 | Powell, III et al. . |
| 5,423,872 | 6/1995 | Cigaina . |
| 5,540,730 | 7/1996 | Terry, Jr. ................... 607/40 |

FOREIGN PATENT DOCUMENTS 129483  12/1984  European Pat. Off. .......... 607/40

OTHER PUBLICATIONS

Bilgutay et al., "Gastrointestinal Pacing a New Concept in the Treatment of Ileus", Biomedical Sciences Instrumentation, vol. 1, pp. 377–383 (1963).

*Primary Examiner*—Jeffrey R. Jastrzab
*Attorney, Agent, or Firm*—Whitham, Curtis, Whitham & McGinn

[57] ABSTRACT

A portable or implantable gastric pacemaker includes multiple electrodes that are positionable on the inner or outer surface of an organ in the gastro-intestinal tract and which are individually programmed to deliver a phased electrical stimulation to pace peristaltic movement of material through the GI tract. The pacemaker will accommodate variations in pulse amplitudes, pulse durations, pulse periods, and relative pulse phasing among the electrodes. Computer control can be used to adjust and vary all stimulation parameters delivered by the electrodes to achieve effective treatment and re-training of an organ for natural pacing. The pacemaker can be programmed with parameters to enhance or accelerate peristaltic movement through the gastric tract or to attenuate the peristaltic movement to treat such conditions eating disorders or diarrhea.

12 Claims, 4 Drawing Sheets

GASTRO-INTESTINAL PACEMAKER HAVING PHASED MULTI-POINT STIMULATION

BACKGROUND OF THE INVENTION

1. Field of the Invention

The invention generally relates to electronic pacemakers used to stimulate organs in the gastro-intestinal tract, such as the stomach, duodenum, and colon, for the purpose of adjusting gastric or intestinal motility and, more particularly, to a pacemaker which uses multiple electrodes to stimulate multiple sites on a single organ or on different sites on multiple organs in the gastro-intestinal tract in a controlled fashion which will adjust gastric or intestinal motility to treat a variety of different gastric and intestinal disorders.

2. Description of the Prior Art

Material, in the form of edible food and liquids, is directed through the organs in the gastrointestinal (GI) tract via peristaltic movement. The timing of the contractions of each of the organs is controlled by a physiological mechanism. The gastric "slow wave" in the normal human stomach, which is the contraction propagation frequency in the stomach, is reported to be approximately three cycles per minute. Other organs in the GI tract normally have different propagation frequencies. For example, it is believed that the frequency at the top of the duodenum is approximately 12.5 cycles/minute, and the frequency more distally in the small bowel, is approximately 9 cycles/minute (cpm).

Abnormalities in myoelectric activity in the GI tract can result in a variety of disorders harmful to human subjects. For example, gastroparesis exists when a patient experiences delayed gastric emptying. Conversely, dumping syndrome and some diarrhia states may be caused by gastric emptying which is too quick. Constipation results when the colon fails to move fecal matter properly. By contrast, chronic dumping syndrome, short bowel syndrome, and idiopathic diarrhea may be the result of the colon moving matter too quickly. Table 1 identifies a number of different clinical conditions which result from irregular gastric and intestinal myoelectric activity.

TABLE 1

Tachygastrias (4–9.9 cpm myoelectrical pattern-freguency higher than normal)

Gastroparesis (diabetic, idiopathic, ischemic)
Intestinal pseudo-obstruction
Nausea of Pregnancy
Functional dyspepsia-dysmotility type with normal gastric emptying
Gastric Ulcers (acute) with nausea
Postoperative; acute post-op with ileus; Post-cholecystectomy
Eating disorders-anorexia nervosa
Premature infants
Drug-induced (glucagon, epinephrine, morphine sulfate)
Functional (idiopathic) dyspepsia with delayed gastric emptying
Tachyarrhythmias (mix of tachygastrias and bradygastrias)

Motion sickness
idiopathic gastroparesis
Bradygastrias (1–2 cpm myoelectrical pattern-freguency normal)

Gastroparesis (diabetic, idiopathic, ischemic, post-operative (gastric resection))
Intestinal pseudo-obstruction
Nausea of Pregnancy
Functional dyspepsia-dysmotility type with normal gastric emptying
Eating disorders-bulimia nervosa
Drug induced-epinephrine

TABLE 1-continued

Arrhythmias (no discernible rhythm)

Nausea of pregnancy
Hyperemesis gravidarum
Drug induced epinephrine
Bilroth I or II with gastroparesis
Bilroth I or II with dumping syndrome
Colon Short bowel syndrome (not necessarily abnormal myoelectric activity)
idiopathic diarrhea (not necessarily abnormal myoelectric activity)
irritable bowel syndrome secondary to a motility disorder (not necessarily abnormal myoelectric activity)
constipation (not necessarily abnormal myoelectric activity)
Roux-en Y reconstructions (10–13 cpm small bowel frequencies)

Pacemakers have been used for many years in cardiac care. These devices are typically implantable, and include control circuitry and electrodes that stimulate the heart tissue on a regimented basis. Pacemakers have been suggested for use in pacing the stomach; however, the level of understanding of stomach pacing is not as well developed as cardiac pacing. In addition, the requirements for effective stomach pacing are quite different from those for cardiac pacing. Ideally, a gastric pacemaker should deliver electrical signals to mimic natural gastric signals.

U.S. Pat. No. 3,411,507 to Wingrove discloses a device for gastrointestinal stimulation which uses an electrode positioned on a nasogastric catheter and an electrode secured to the abdominal wall. In operation, the nasogastric catheter is inserted into the patient's stomach while the patient is laying down. The electrode is positioned in close proximity to the pylorus of the stomach. To institute peristaltic activity, the patient is preferably given an electrical stimulation for the first five seconds of every minute until positive results are obtained. The electrical stimulation is for a period of 0.1 milliseconds (ms) every 25 ms of the first five minutes. Wingrove also discloses using electrical stimulation of the same order of magnitude as the normal range of periodicity of the inherent peristaltic pacemaker action of the duodenum. The stimulation process is discontinued after the first bowel movement. Wingrove suffers from the disadvantage of only being a short term device. That is, it is only useful for patients in a hospital setting, and particularly patients that are laying down. Wingrove offers no long term solution to patients with digestive disorders. In addition, Wingrove does not allow for adjusting the electrical stimulation to suit the needs of a particular patient.

U.S. Pat. No. 5,292,344 to Douglas discloses a percutaneously placed electrical gastrointestinal pacemaker which provides for stimulation, sensing, delivery of fluids and nutrients, and pH sensing. The Douglas device can be used to treat a wide variety of gastric disrhythmias and can be used for both short and long term patient care. In operation, a plurality of electrodes are percutaneously and endoscopically placed on the inner lining of the gastrointestinal tract. The electrodes are all simultaneously pulsed with the same current and pulse rate. The current and pulse rate are adjustable by both mechanical and electrical systems. A pH sensor and a pressure sensor are connected inside the stomach, and are used for analysis of the electrical stimulation effects. Control circuitry is used in a feedback loop to control the timing of pulses. For example, if a response to the electrical stimulation is delayed beyond a controllable time threshold, a signal is given to provide another stimulative pulse. In addition, the control circuitry can be used to uniformly adjust the strength of the pulse, and to alert primary care providers of possible dangers. The Douglas gastric pacemaker provides several advantages. First, it is portable, and can be worn by a patient during day-to-day activities. Second, it allows for long term pacing. Third, it provides multiple electrodes and feedback elements. However, the Douglas system requires intense signals to be delivered to one region of the stomach, and does not address frequency cancellation problems which can occur when multiple sites are stimulated simultaneously.

Several other U.S. patents show the use of electrical stimulation of organs. For example, U.S. Pat. No. 5,188,104 to Wernicke et al. discloses stimulation of the vagus nerve for the treatment of eating disorders such as compulsive over-eating, bulimia, or anorexia nervosa. Wenicke et al. does not discuss the treatment of gastric motility disorders or the restoration of normal gastric peristalsis. U.S. Pat. No. 5,423,872 to Cigaina discloses stimulating a single electrode pair affixed to the stomach for the purpose of decreasing the frequency of the gastric slow wave. The Cigaina device is used for treating obesity and other over eating disorders. U.S. Pat. No. 4,921,481 to Danis is related to a process for monitoring the frequency of gastric myoelectric signals to aid in the correct placement of gastric feeding tubes. U.S. Pat. No. 5,197,491 to Anderson describes a technique for placing an electrode into a patient's stomach adjacent to the heart for cardiac stimulation.

SUMMARY OF THE INVENTION

It is an object of this invention to provide an implantable or portable gastro-intestinal pacemaker which utilizes phased, multi-point electrical stimulation of organs in the gastro-intestinal tract, such as the stomach, intestines (duodenum), bowels, and colon.

According to the invention, an implantable or portable gastrointestinal pacemaker having specific application to gastric pacing, but having general application to pacing any organ in the gastro-intestinal tract through which peristaltic movement of material is controlled by natural electrical pacing (e.g., intestines, bowels, colon, etc.), includes multiple electrodes that are positionable at multiple sites on a single organ in the gastro-intestinal tract or on different sites on different organs in the gastro-intestinal tract, and an electronic controller which regulates the pulse amplitudes, pulse durations, pulse periods, and relative pulse phasing among the electrodes. The electronic controller should be programmable to allow adjusting the stimulation parameters for treating different disorders in the gastro-intestinal tract, as well as adjusting the stimulation parameters based on individual patient performance in response to gastro-intestinal stimulation. Feedback from the gastro-intestinal tract can be provided by incorporating one or more sensor electrodes which can sense the strength of contraction of one or more organs in the gastro-intestinal tract in response to the electrical stimulation provided by the other electrodes. The amplitude of the pulse stimulation or the relative pulse timing can be adjusted if the contractions are too strong or too weak. Ideally, the same electrodes can be used for both stimulating an organ in the gastro-intestinal tract and sensing the response of the organ by providing a duty cycle in the electronic controller which calls for sensing pressure differences or organ movement due to contractions during periods when the electrode is not providing a signal pulse to the organ. In the preferred embodiment, the stimulation parameters of each of the electrodes is independently adjustable by the electronic controller, thus allowing the phasic relationship of the electrodes to be controlled relative to all other electrodes, and allowing the amplitude to be modified in accordance with individual patient responses, as well as providing other advantages. In the case of an implanted pacemaker, the electronic controller will ideally be programmable using an inductive coupling methodology, radio communication methodology, or some other suitable means. In the case of a portable pacemaker, the electronic controller preferably will be provided with an interface which can be directly coupled to a computer system for interrogation of stored data related to contractions and programming of each electrode. Low-cost, pre-programmed versions of the pacemaker are also envisioned, wherein the pacemaker will be provided with a program which presets the amplitude, stimulation timing, and phasic regimen. The electrodes preferably are implanted on the inner or outer surface of the stomach or other organ in the gastro-intestinal tract, and, in the case of a portable pacemaker, can preferably be detached from the pacemaker to allow easier interfacing. The electrodes can be collected together using a wiring harness for easier and better connections to the pacemaker.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
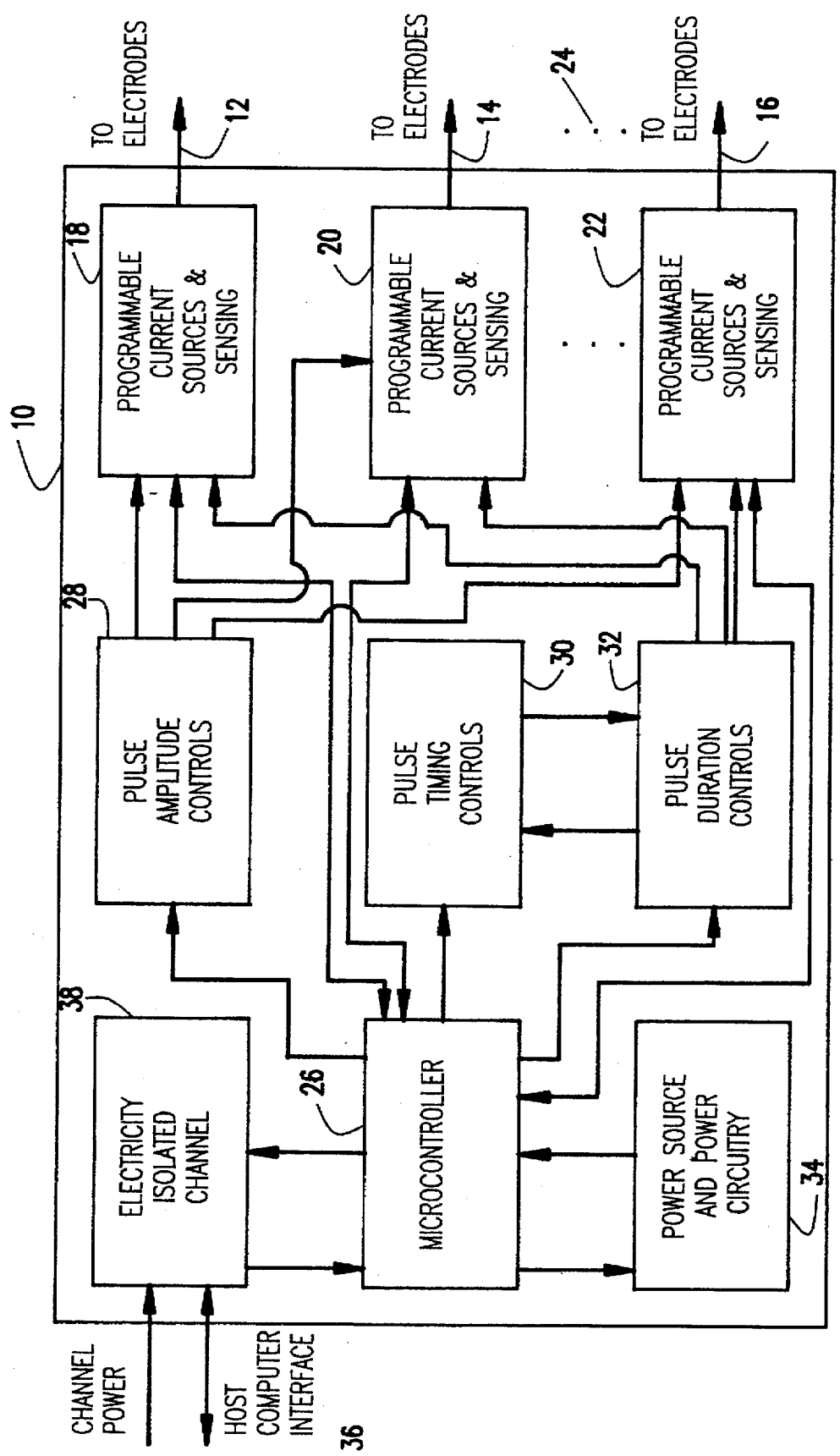
FIG. 1 is a schematic diagram of a preferred pacemaker according to the present invention.

FIG. 1 shows a pacemaker 10 according to the present invention which includes multiple electrode connectors 12, 14, and 16. Each electrode (not shown) has a programmable current source 18, 20, and 22 for delivering a selected level of current at a selected time for a selected duration. The three dot pattern 24 indicates that several other electrodes can be connected to and controlled by the pacemaker 10. In the case of additional electrodes, additional programmable current sources can be provided, or, alternatively, a single programmable current source can be used to control the amplitude, pulse duration, and phasic relationship of all electrodes. A microcontroller 26 positioned in the pacemaker 10 is used for adjusting and controlling the electrical stimulation provided by the pacemaker 10 to an organ of interest. The micro controller 26 can individually set current, timing, and pulse duration parameters for each programmable current source 18, 20, and 22, using pulse amplitude controls 28, pulse timing controls 30, and pulse duration controls 32. Hence, each of the electrodes can deliver the same strength pulse, for the same time, for the same duration, if desired. However, it is expected that in most applications where peristaltic flow through an organ in the gastro-intestinal tract is desired, the pulse strength, phase, and duration will need to be adjusted for each electrode relative to one another.

A power source and associated circuitry 34 is positioned within the pacemaker 10 to maintain power to the microcontroller 26 and to power the electrical stimulations delivered to each of the electrodes. In the preferred mode of operation, the pacemaker 10 is a portable unit which can be worn by the user with a belt or other support device. Alternatively, the pacemaker 10 may be an implantable unit similar to a cardiac pacemaker. In either configuration, the power source 34 should be suitable for providing power for an extended period of time, and will preferably be rechargeable. Extended life batteries are preferred for use as the power source 34. In the case of an implanted pacemaker 10, the power source 34 should be chargeable through inductive coupling or a similar source outside of the patient's body. To enhance portability, the electrode connectors 12, 14, and 16, should be collected into a harness and be detachable from the electrodes (not shown).

Figure 2:
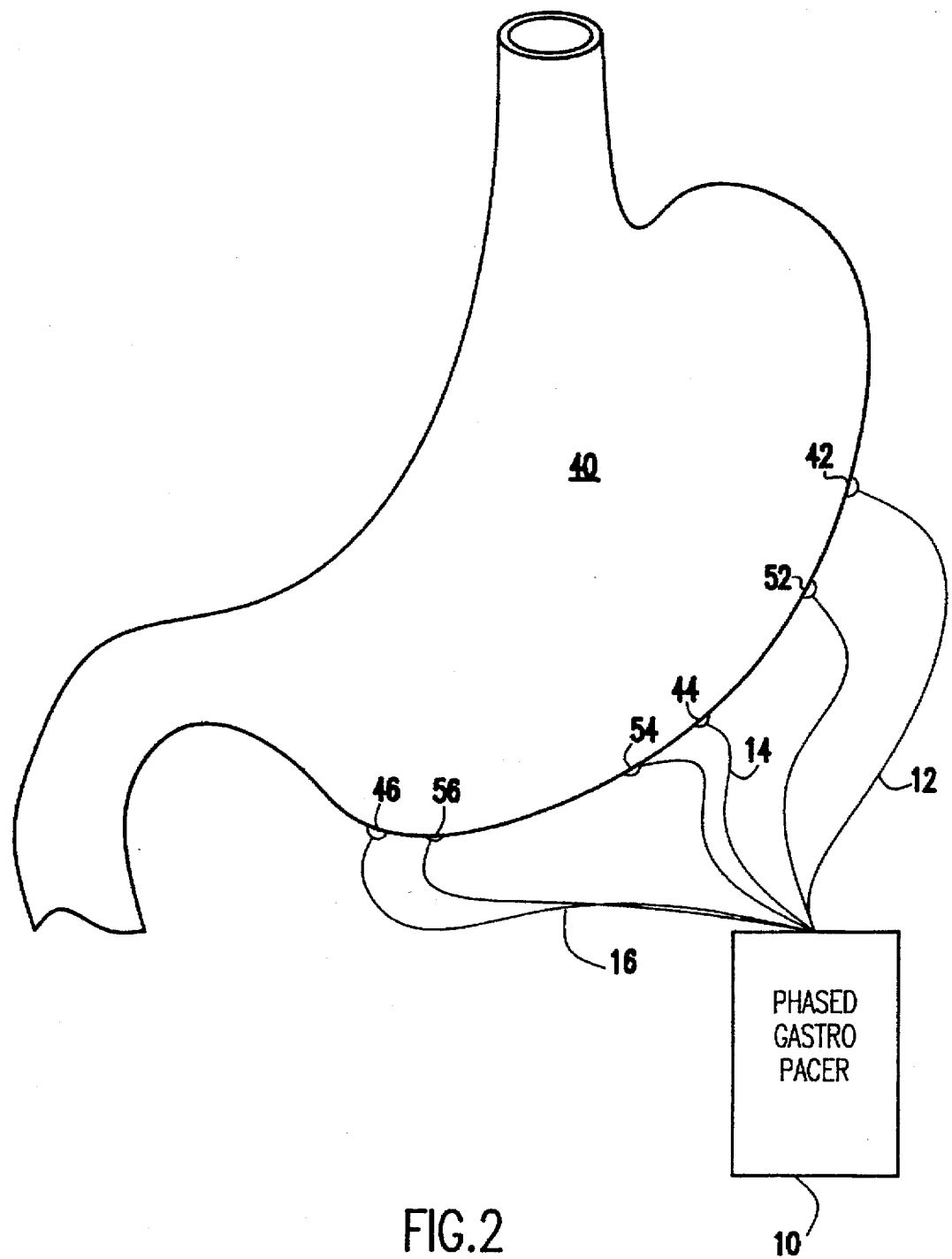
FIG. 2 is a representative drawing of the human stomach showing the phased gastric pacemaker of the present invention and one possible arrangement for placement of the electrodes for delivering phase pulsed electrical stimulation.

The electrodes are preferably implantable on the inner or outer surface of the gastro-intestinal tract organ, and should be of a sufficient length that they can be connected at different locations. For example, FIG. 2 shows several stimulation electrodes 42, 44, and 46, as well as sensor electrodes 52, 54, and 56, positioned on the outer curvature of a human stomach. It should be understood by those of ordinary skill in the art that electrodes can be implanted on different organs which require peristaltic flow of material (e.g., colon, intestines, bowels, etc.), and that a single pacemaker 10 can control different electrodes implanted on different organs (e.g., stomach and intestines). In all configurations, this invention contemplates the use of multiple electrodes (at least two) positioned at multiple sites (either on the same organ or different electrodes positioned on different organs).

With reference back to FIG. 1, the microcontroller 26 can be programmed, as well as interrogated by a host computer (not shown) to evaluate performance, using a host computer interface 36 selectively connectable to the microcontroller 26 using an electrically isolated channel 38 or by other means. In the case of an implantable pacemaker 10, the host computer interface 36 will preferably be accomplished using radio frequency (RF) transmissions, inductive coupling, or other communications technologies. In operation, the pacemaker 10 will be programmed using the host computer interface 36 at a clinic, hospital, or other care facility, or will be programmed at the time of sale or patient installation or implantation to provide certain electrical outputs depending on the application of the pacemaker and the disorder being treated.

FIG. 2 shows that other sensors can be connected to the organ of interest to assist in proper programming and operation of the pacemaker 10. In the arrangement shown in FIG. 2, the electrical stimulation applied to one region of the stomach by stimulation electrodes 42, 44, or 46 will cause contractions which are sensed by sensor electrodes 52, 54, and 56. Depending upon the strength of the contractions sensed by the sensor electrodes (52, 54, and 56), the pulse amplitude and duration to be used for stimulation by each individual electrode 42, 44, and 46 can be adjusted, and the phasic relationship of the pulses from electrodes 42, 44, and 46 can be adjusted. This sensed information can be provided to the host computer through the interface 36 connected to microcontroller 26, and, will preferably be used directly in a feedback loop program in microcontroller 26. In this way, the responses of different patients to different electrical stimuli can be adjusted. The response of an organ in the gastro-intestinal tract to different electrical stimulations at different regions of an organ, can also be monitored and used to provide feedback to program each of the programmable current sources 18, 20, and 22 to respond in a concerted, phased mode of operation. In addition, after use of the pacemaker for a period of time, the performance of the pacemaker 10 can be evaluated in detail by downloading to the host computer through the interface 36 all the sensed information from the sensor electrodes 52, 54, and 56 and comparing this information with the stimulation parameters used for each of the programmable current sources 18, 20, and 22.

While FIG. 2 shows each electrode 42, 44, and 46, paired with a sensor electrode 52, 54, and 56, it should be understood by one of ordinary skill in the art that a single sensor could be provided to monitor the contractive response of the entire organ, or that the individual electrodes 42, 44, and 46 might also be used intermittently as sensors using a duty cycle which allows stimulation by the electrode during certain periods and sensing by the electrode during other periods. Alternatively, the pacemaker 10 could be used without sensors 52, 54, and 56, and adjustments to the pulse amplitude, duration, and phasic relationship between electrodes can be programmed based solely on the individual patient's perceived experiences.

In a particular embodiment of the invention, the pacemaker is used to stimulate the stomach of a patient for the purpose of improving gastric emptying. Periodic phased pulses of electric current having controlled amplitude and duration are delivered to electrodes implanted on the surface of the stomach. However, it should be understood that the pacemaker and methodology of this invention is applicable to all organs in the gastro-intestinal tract including the colon, bowel, and duodenum (intestines), and that a variety of different disorders, and particularly those discussed above in Table 1, can be treated. The patient, the organ to which the electrodes are connected, and the disorder being treated will all affect the programmed pulse amplitude, duration, and timing for the electrodes. The pacemaker of this invention ideally can adjust the amplitude, duration, and timing of stimulation for every electrode, such that the pacing regimentation applied to an organ is phased to achieve the desired result. The invention can be used beneficially in both human and veterinary applications.

In the normal human stomach, the gastric slow wave is approximately 3 cpm. In addition, the upper portion of the duodenum has a frequency of approximately 12.5 cpm, the lower portion of the lower intestine has a frequency of approximately 9 cpm, and the colon has a frequency of approximately 9 cpm. This invention contemplates treating disorders where peristaltic flow has slowed or stopped (e.g., gastroparesis in the stomach; constipation in the colon, etc.) by pacing the organ with electrical stimulations that have a frequency that is equal to or greater than the natural frequency; approximately 10% greater is preferred and 5-20% greater should provide optimum results. For example, in the case of gastroparesis, electrodes connected to the stomach should be pulsed in a phased fashion to provide a wave of approximately 3.3 cpm, or in the case of constipation, electrodes connected to the colon could be pulsed in a phased fashion to provide a wave and rhythm variation normally present in the different segments of the colon. Conversely, the invention, contemplates treating disorders were peristaltic flow is too fast with a retrograde, phased pacing which overrides the natural pacing rate for the organ. Optimum results can be obtained with pulsing frequencies that are 10–400% greater than the normal frequency wave for the organ. For example, in treating obesity, one might apply retrograde, phase pacing of 3.3 to 12 cpm to electrodes positioned in or on the stomach; thereby overriding the natural peristaltic flow through the stomach. Likewise, in treating small bowel syndrome, one might apply retrograde, phase pacing of 9.9 cpm or more to the bowel.

Experiments have shown that single point electrodes delivering pulses having a pulse amplitude of 1–4 mA and pulse duration of 100–300 ms are sufficient to pace and retrain the stomach for peristaltic movement therethrough, and particularly to treat patients suffering from gastroparesis. It is expected that the 1–4 mA pulse amplitude and the 100–300 ms duration can be varied significantly and that, within the practice of this invention, organs in the gastrointestinal tract can be stimulated with an electrical signal from each of the electrodes which as a pulse amplitude ranging from 0.1 mA to 10 mA and a pulse duration ranging from 10 µs to 1000 ms, however, in certain situations a pulse amplitude or pulse duration outside of the specified ranges may also be useful.

A particular advantage of using multiple site, phased, electrical stimulation, is that lower levels of current are likely to be satisfactory (e.g., 0.1–2 mA) since the phased relationship of the signals will be additive in effect on the organ. Use of multiple sites which are stimulated simultaneously suffers from the drawback of having the stimulatory effects of one or more electrodes canceling out the stimulatory effects of one or more different electrodes. By adjusting the phase, timing and duration of the pulse provided by each electrode a peristaltic wave originating at the top of an organ can progress smoothly and build gradually as it travels down the organ. In this way, the wave will not be slowed or canceled by out-of-phase interactions. Conversely, if retrograde or reverse material movement is desired or it is desired to slow down the natural peristaltic wave in an organ in the GI tract in the treatment of a disorder (e.g. obesity, chronic dumping syndrome, etc.), controlled, phased, pulsing of the organ can be used to overcome the natural peristaltic flow in the organ.

Figure 3:
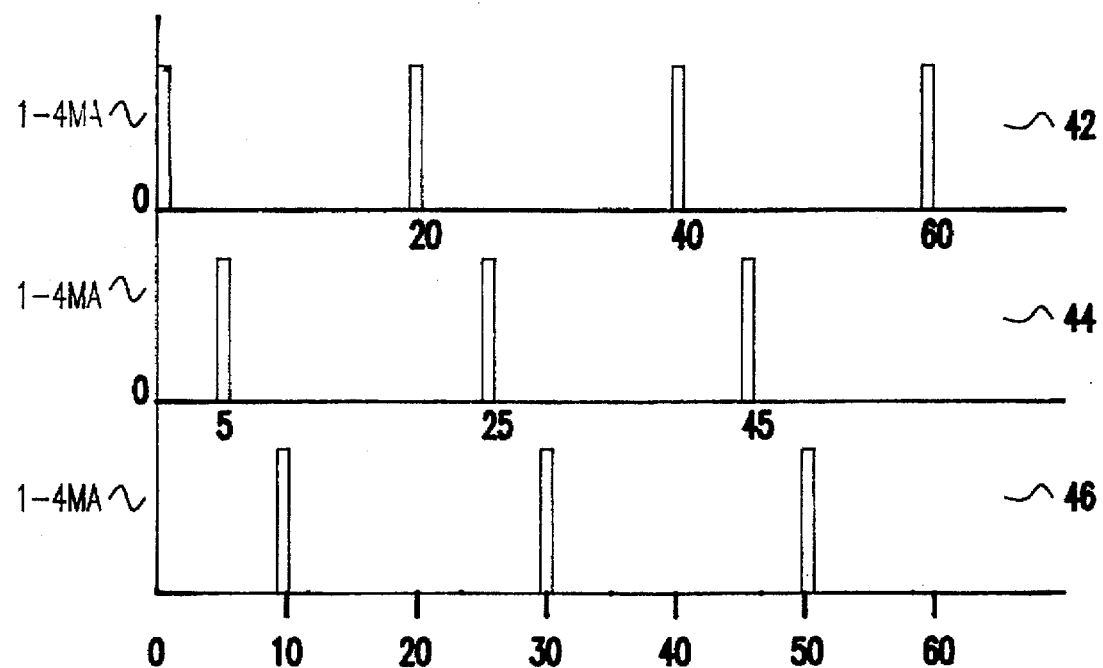
FIG. 3 is a graph showing a forward phased pulsing regime.
Figure 4:
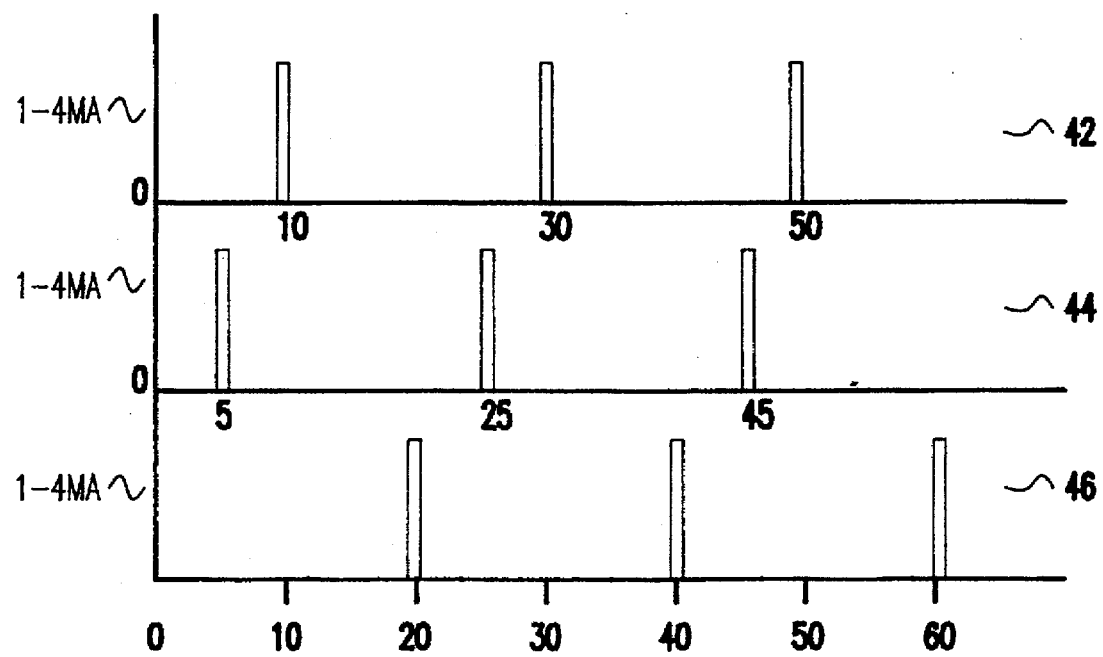
FIG. 4 is a graph showing a retrograde or reverse phased pulsing regime.

FIGS. 2–4 describe the phased pacing contemplated by this invention wherein the pacemaker includes a controller that can adjust the pulse strength, duration and timing to achieve a phased relationship between the electrodes at multiple sites on organ(s) in the GI tract. As shown in FIG. 2, the stomach has a natural gastric slow wave pacing regime of about 3 cycles per minute. However, the gastric slow wave propagates distally toward the pylorus with increasing frequency and amplitude. Hence, the stimulation provided by the discrete electrodes positioned along the stomach wall are preferably controlled to sequentially provide pulses of increasing frequency and amplitude. Three electrodes 42, 44, and 46, are shown connected to an upper, mid, and lower portion, respectively, along the outer curvature of a human stomach 40. The electrodes 42, 44, and 46, are connected to the phased gastric pacer unit 10 by electrode connector leads 12, 14, and 16, respectively.

As shown in FIGS. 3 and 4, the pulsing of electrodes 42, 44, and 46 are phased relative to one another. For example, in the case where electrodes 42, 44, and 46 are paced to stimulate the stomach at 3.0 cycles per minute (cpm) as shown in FIG. 3, electrode 42, at the top of the stomach pulses at 0, 20, 40 and 60 seconds, electrode 44, positioned at the mid point in the stomach, lags the pulse from electrode 42 by 5 seconds, pulsing at 5, 25, and 45 seconds, and electrode 46, positioned at the lower point in the stomach, lags the pulse from electrode 44 by 5 seconds, pulsing at 10, 30, and 50 seconds. As shown by example in FIG. 3 the pulses have an amplitude of 1 to 4 mA and a duration or width of 100 to 300 ms. Both of these parameters can be adjusted up or down depending on the patient and the treatment, and, as indicated above, the pulse amplitude preferably ranges from 0.1 mA to 10 mA, and the pulse duration preferably ranges from 10 milliseconds to one second (e.g., longer pulse durations of approximately one second and/or stronger signals of approximately 10 mA may be advantageous in certain situations, while shorter pulse durations of 10 milliseconds and/or weaker signals of approximately 0.1 mA may be advantageous in other situations).

It is noted that the above example is but one phased gastric pacing regime. For instance, if more than three electrodes are used, a similar phased pacing regime could be used with each electrode having a smaller phase shift relative to adjacent electrodes. Also, the lag time of the preceding electrodes may be adjusted depending on the particular patient or application. Likewise, the 3 cpm regime specified in the examples may be altered depending on the patient and the particular treatment sought. For example, in the case of the stomach having a natural slow wave cycle of 3 cpm, the pacemaker of the present invention may be adjusted to stimulate a cycle in the range between 90% to 400% of the natural frequency or 2.7 cpm to 12 cpm, respectively. As discussed above, optimum results can be achieved when the pacing is 5–20% greater than the natural frequency (e.g., 3.15 cpm to 3.6 cpm in the stomach for treating gastroparesis). Placement of the electrodes can also impact on the pulse amplitude, duration, and phasic relationship. For example, in an arrangement where the electrodes are positioned 2–3 cm apart on the organ in the GI tract, a 5–10 second interval between stimulations provided by adjacent electrodes should provide satisfactory results; however, when the electrodes are positioned 10 cm apart or more, both the amplitude of the pulse and the time between electrical pulses by adjacent electrodes should be greater. It is preferred that the electrodes be positioned between 1 cm and 20 cm apart to achieve the phased pacing contemplated by this invention, and preferably between 1 and 5 cm apart.

In certain situations, it is desirable to slow down or attenuate gastric emptying. For example, one could hypothesize for an obese person that food is passed from the stomach into the small intestine at a relatively fast rate thereby causing the person to feel hungry and encouraging additional caloric intake beyond that which is necessary for good health. Hence, it could be advantageous to prolong the time food is kept in the obese patient's stomach to promote a prolonged "full" feeling and discourage further food intake. Additionally, if there is rapid small bowel transit or "dumping" then disrupting this movement with retrograde pacing could be good therapy.

This invention contemplates programming the pacemaker with a retrograde or reverse phased regime whereby the phased pacing is selected to work against the natural pacing of the organ. Thus, in the retrograde mode the natural gastric slow wave is actually canceled to some degree to slow down the stomach emptying process. FIG. 4 shows an example of a reversed phased regime, again for 3 cpm. Here, electrode 46, at the bottom of the stomach pulses first at 0, 20, 40 and 60 seconds. Electrode 44, positioned at the mid point in the stomach, lags the pulse from electrode 46 by 5 seconds, pulsing at 5, 25, and 45 seconds. Likewise, electrode 42, positioned at the upper point in the stomach, lags the pulse from electrode 44 by 5 seconds, pulsing at 10, 30, and 50 seconds. The pulses may have an amplitude of 0.1 to 10 mA and a duration or width of 10 to 1000 ms which can be evaluated and adjusted accordingly. Given the strong natural pacing characteristics of the stomach, it may be advantageous to program the pacemaker to deliver stronger electrical signals at a considerably faster rate (e.g., 8–12 cpm) to override the natural peristaltic flow through the stomach. As discussed above, more or less electrodes could be used in the practice of retrograde pacing, and the positioning of electrodes can vary between 1 cm and 20 cm apart.

Figure 5:
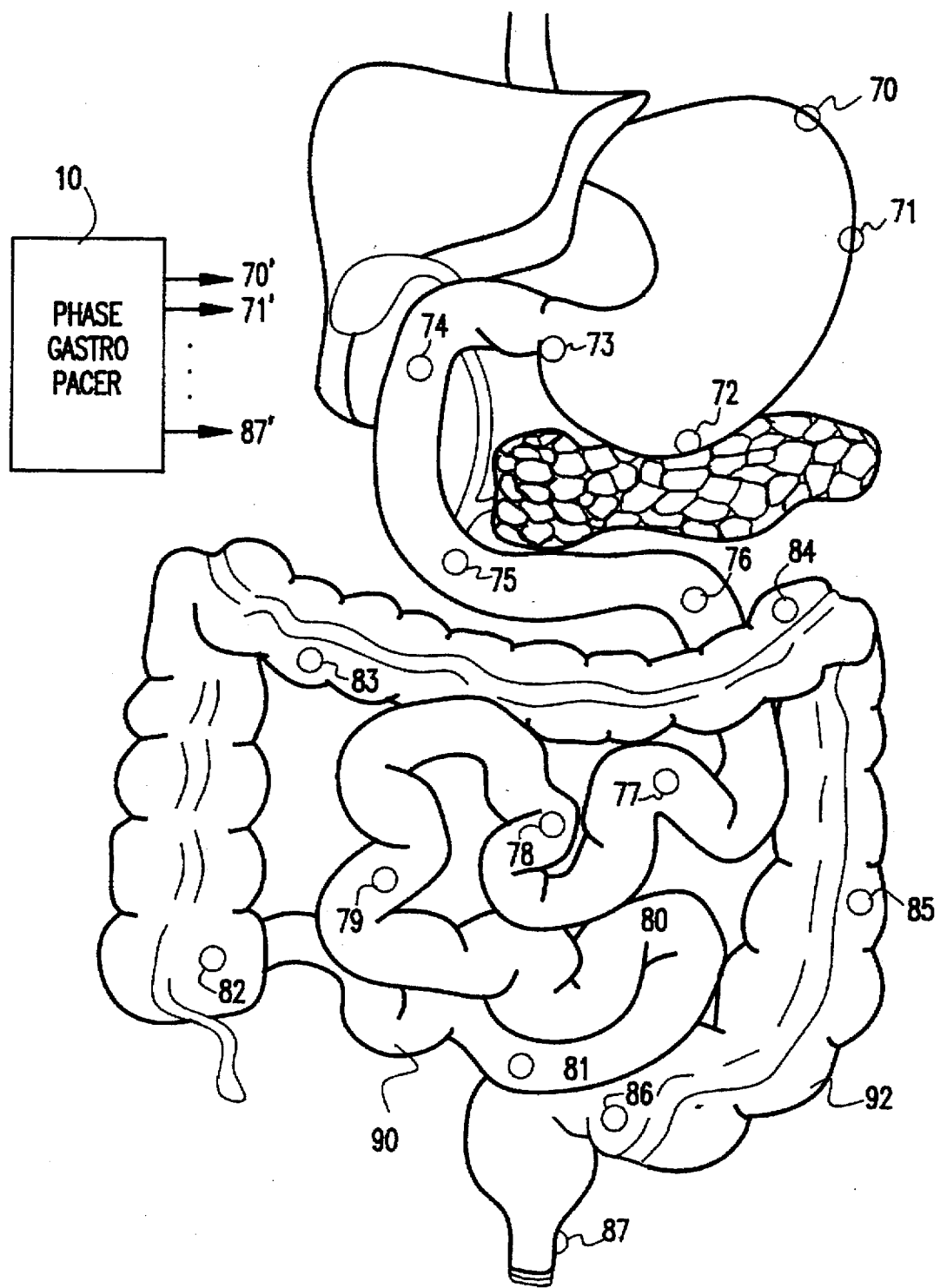
FIG. 5 is a diagram of the human gastric tract showing phased pacemaker electrodes connected to the stomach, small intestine, large intestine, and colon.

FIG. 5 is a diagram of the human gastric tract showing the phased pacemaker having a plurality of electrodes 70–87 connected to the digestive organs including the stomach 88, the small intestine 90, and the large intestine and colon 94. The phased gastric pacemaker 10 of the present invention has a plurality of leads 70'–87' connecting each of the electrodes 70–87 to a corresponding programmable current source (as shown in FIG. 1). The electrodes 70–87 are programmed to provide phased, multipoint electrical stimulation for achieving peristaltic flow through the digestive tract.

As mentioned above, the various digestive organs each have a natural peristaltic cycle, such as the human stomach which is typically 3 cycles per minute. However, it is contemplated that in certain applications it may be beneficial to pulse the electrodes at different cycle frequencies for the various organs. For example, in the stomach 88 the frequency of the cycle may decrease from the natural pacing cycle of 3.0 cpm at top electrode 70 to 4 cpm at electrode 72 positioned at the lower stomach. In this scenario, mid-positioned electrode 71 may have a frequency of 3.5 cpm and each of the electrodes may deliver a pulse of increasing amplitude and duration. Similarly, in the small intestine 90, the first electrode 73 positioned at the duodenum may be pulsed at a frequency of 12.5 cpm decreasing to a frequency of 9 cpm at the last electrode 81. In addition, a weaker amplitude pulse for a shorter duration may be used in the small intestine than was required in the stomach. For example, a 1–2 mA pulse may be used having a duration or width of only 50–100 ms.

Similarly, as shown in FIG. 5, the colon 90 has a plurality of electrodes 82–87 connected along its length which can be pulsed in a phased manner to provide multipoint electrical stimulation for achieving a desired peristaltic flow. A malfunctioning colon may be the source of many common bowel problems. Such problems include diarrhea, a pathological excessive evacuation of watery feces, at one extreme, and constipation, the difficult or infrequent evacuation of the bowels, at the other extreme. The gastric pacemaker of the present invention having phased multipoint electrical stimulation can help to abate both of these problems.

For example, in the case of constipation, the pacemaker can be programmed to induce an accelerated pacing regime, for example, 10–20% above the natural pacing rhythm of the colon. With an accelerated rhythm, bowel evacuation can be enhanced. Similarly, in the case of diarrhea, dumping syndrome, or irritable bowel syndrome, the pacemaker can be programmed to induce a retrograde pacing which, similar to the obesity example above, the pacing program is calculated to work against the natural pacing rhythm of the colon such that the natural pacing rhythm is canceled by some degree thereby delaying and better controlling bowel evacuation.

A preliminary study was conducted with a series of experiments with different stimulus patterns using a single pair of electrodes positioned on the outer curvature of the stomach on five patients with gastroparesis to optimize the performance of the gastric pacing. A portable gastric pacemaker with optimal pacing parameters was given to each patient to use at home daily for one month. Gastric emptying results before and after long term pacing was compared.

The study was performed on five patients (one male, four females with a mean age of 42) with gastroparesis undergoing abdominal surgery for the placement of a feeding jejunostomy tube. Four pairs of bipolar electrodes were placed on the serosa of the stomach along the greater curvature at an interval of 2–3 cm during surgery. The electrodes were gauge stainless steel cardiac pacing wires (available from A&E Medical of Farmingdale, N.J.). The wires were brought out through the abdominal wall percutaneously. The top pairs of electrodes were used for delivering electrical stimulation while the rest was used for recording gastric electrical activity.

The initial study on electrical stimulation was performed one month or more after the surgical procedure when the patients were recovered from the surgery and able to eat. After a baseline recording of 60 minutes, electrical stimulation was performed in a number of sessions with different pacing parameters, each lasting for thirty minutes.

The waveform of the electrical stimuli used was periodic rectangular pulses with a width of 0.3 seconds which were generated by a commercially available unit (WPI model A310), isolated by a WPI isolator, model A350D. The frequency of stimuli was varied from 10% lower to 400% higher than the intrinsic gastric slow wave frequency of 3 cycles per minute (e.g., 2.7 to 12 cycles/minute). The amplitude was varied from 1 mA to 4 mA at different frequencies to test the effect of pacing parameters on gastric myoelectrical activity. As is explained above, it is preferable to use a pacemaker where each of a plurality of electrodes can be individually programmed and adjusted to provide an optimum pulse strength and pulse width.

For long term gastric pacing, after the initial study on optimization of pacing parameters, patients were given the portable pacemaker to use at home daily for one month. The patients were asked to turn on the electrical stimulation thirty minutes before eating, and to turn off the electrical stimulation two hours after each meal. The patients all completed a symptom form on a daily basis which included their feelings after each meal and symptoms of the day. At the end of one month, a gastric emptying study was performed using the same meal as used for the baseline on each of the patients to assess the effect of long-term electrical stimulation on gastric emptying.

At a pacing frequency of 10% higher than the intrinsic gastric slow wave frequency (IGF) (approximately 3.3 cycles per minute), the gastric slow wave in all patients was completely retrained to approximately 10% higher with a pacing strength of 4 mA, and partially retrained to $7.4\pm1.6\%$ higher with 2 mA and $4.8\pm1.7\%$ higher with 1 mA. Pacing at a frequency of four times higher than the IGF (e.g., approximately 12 cycles per minute) increased the frequency of the slow wave by $22.6\pm4.6\%$. Pacing at a frequency of 10% lower than the IGF (approximately 2.7 cycles per minute) was not able to retrain the gastric slow wave, but reduced the frequency of the slow wave by $1.5\pm1.6\%$. An increase in the amplitude of slow wave was found in three patients during pacing and an increase in the conduction velocity of the slow wave in the proximal antrum of all patients.

Four patients showed delayed gastric emptying in the initial study. The gastric emptying and symptoms were consistently improved in these patients one month after gastric pacing with the portable pacemaker (T½ emptying rate: $506.5\pm161.9$ vs $198.0\pm41.2$ min, p=0.09, t-test; retention at 120 min: $82.3\pm4.5\%$ vs. $70.5\pm5.8\%$, p<0.05, t-test).

The results of this study clearly demonstrate that long-term gastric pacing with the portable gastric pacemaker is able to retrain the gastric slow wave and improve gastric emptying in patients with gastroparesis.

While the invention has been described in terms of its preferred embodiments, those skilled in the art will recognize that the invention can be practiced with modification within the spirit and scope of the appended claims.

We claim:

1. A method for electrically stimulating at least one organ in the gastro-intestinal tract for peristaltic movement, comprising the steps of:

connecting a plurality of electrodes to at least one organ in the gastro-intestinal tract of a patient along a peristaltic flow path, each of said plurality of electrodes being connected at a different location along said peristaltic flow path; and providing electrical pulses to said organ from each one of said plurality of electrodes, said electrical pulsed provided by said plurality of electrodes being in a phased relationship according to a desired peristaltic flow through said at least one organ in said gastrointestinal tract.

2. The method of claim 1 further comprising the step of independently regulating a pulse amplitude, a pulse timing, and a pulse duration for said electrical pulses for each one of said plurality of electrodes.

3. A method for electrically stimulating an organ as recited in claim 2 wherein said organ is a stomach and further comprising the step of selecting a pulse amplitude in the range of 0.1 to 10 mA and a pulse duration in the range of 10 to 1000 ms for at least one electrode of said plurality of electrodes.

4. A method for electrically stimulating an organ as recited in claim 1 wherein said organ is a stomach and further comprising the step of selecting a pulse frequency of 1.5 to 4 cycles per minute for each electrode in said plurality of electrodes with a selected phase offset between adjacent electrodes.

5. A method for electrically stimulating an organ as recited in claim 1 wherein said organ is a small intestine and further comprising the step of selecting a pulse frequency of 9 to 12.5 cycles per minute for each electrode in said plurality of electrodes with a selected phase offset between adjacent electrodes.

6. The method of claim 1 further comprising the steps of:

locating said plurality of electrodes on said organ with at least a first electrode being relatively closer to a distal end of said gastrointestinal tract than a second electrode and said second electrode being relatively more forward in said gastrointestinal tract than said first electrode; and developing a phased pulse regimentation of said organ which progresses from said first electrode to said second electrode.

7. The method of claim 6 wherein said second electrode provides a relatively higher amplitude pulse stimulation to said organ than said first electrode.

8. The method of claim 1 further comprising the steps of:

locating said plurality of electrodes on said organ with at least a first electrode being relatively closer to a distal end of said gastrointestinal tract than a second electrode and said second electrode being relatively more forward in said gastrointestinal tract than said first electrode; and developing a phased pulse regimentation of said organ which progresses from said second electrode to said first electrode.

9. The method of claim 8 wherein said second electrode provides a relatively higher amplitude pulse stimulation to said organ than said first electrode.

10. A gastric pacemaker for controlling the peristaltic pace of digestive organs, comprising:

a plurality of stimulation electrodes sequentially positionable on at least one digestive organ along a peristaltic flow path;

controller for controlling electrical pulse parameters for each of said plurality of stimulation electrodes in a phased relationship according to a desired peristaltic flow; and circuitry for providing electrical pulses to each of said plurality of stimulation electrodes in accordance with said phased relationship.

11. A gastric pacemaker as recited in claim 10 further comprising a sensor electrode connectable to said digestive organ for sensing a response of said organ to an electrical pulse stimulation.

12. A gastric pacemaker as recited in claim 10 wherein at least one of said plurality of stimulation electrodes also functions as a sensing electrode for sensing a response of said organ to an electrical pulse.

* * * * *